United States Patent [19]

Edwards et al.

[11] Patent Number: 4,760,061
[45] Date of Patent: Jul. 26, 1988

[54] ETHER AND ESTER DERIVATIVES OF PHENOLS

[75] Inventors: Philip N. Edwards, Bramhall; Brian S. Tait, Macclesfield, both of England

[73] Assignee: Imperial Chemical Industries PLC, Gerts, England

[21] Appl. No.: 726,823

[22] Filed: Apr. 24, 1985

[30] Foreign Application Priority Data

Apr. 27, 1984 [GB] United Kingdom ............... 8410901

[51] Int. Cl.$^4$ .................. C07C 66/67; A61K 31/22
[52] U.S. Cl. .................. 514/211; 514/212; 514/222; 514/252; 514/255; 514/316; 514/317; 514/319; 514/326; 514/330; 514/331; 514/365; 514/374; 514/399; 514/423; 514/428; 514/478; 514/480; 514/481; 514/483; 514/510; 514/522; 514/548; 514/550; 514/551; 540/163; 540/544; 540/553; 540/596; 540/597; 540/598; 540/602; 540/603; 540/610; 544/58.6; 544/59; 544/60; 544/129; 544/141; 544/158; 544/159; 544/168; 544/171; 544/357; 544/360; 544/365; 544/369; 544/370; 544/372; 544/386; 546/187; 546/189; 546/190; 546/206; 546/208; 546/209; 546/210; 546/226; 548/535; 548/539; 548/540; 548/518; 558/413; 558/414; 558/417; 560/133; 560/138; 560/139; 560/150; 560/151; 560/152; 560/173; 560/185; 560/252; 560/255

[58] Field of Search ............... 560/138, 139, 252, 255, 560/133, 150, 151, 152, 173, 185, 9, 10, 11, 12, 16, 27, 28, 107, 194; 548/518, 535, 539, 540; 546/202, 208, 226, 187, 189, 190, 209, 210, 227, 205, 226, 231, 216; 549/51, 61; 540/602, 607, 163, 544, 553, 596, 597, 598, 603, 610; 514/212, 319, 324, 326, 330, 422, 443, 480, 481, 483, 510, 548, 211, 222, 252, 255, 316, 317, 331, 365, 374, 399, 423, 478, 522, 550, 551, 617, 210, 336, 424, 408, 428; 544/58, 6, 59, 60, 129, 141, 158, 159, 168, 171, 357, 360, 365, 370, 372, 386; 558/413, 414, 417; 562/594, 583, 556, 557; 564/48, 56, 74, 85, 104, 237, 158, 154, 162, 169, 172, 207; 568/29, 31, 33, 43, 49, 327, 328, 325, 329

[56] References Cited
FOREIGN PATENT DOCUMENTS
0124369 11/1984 European Pat. off. .

Primary Examiner—Michael L. Shippen
Attorney, Agent, or Firm—Cushman, Darby & Cushman

[57] ABSTRACT

Mono- or bis-complex esters or ethers of a phenol derivative of the formula

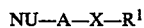

wherein NU is a defined mono- or bis-phenolic nucleus including a hydroxyphenyl-hydroxynaphthyl; hydroxyphenyl-hydroxyindanyl, hydroxyphenyl-hydroxybenzothienyl or di-hydroxyphenyl-ethylene or vinylene nucleus; wherein
A is alkylene, alkenylene or alkynylene which may be interrupted by phenylene or other linkages, wherein $R^1$ is hydrogen, or alkyl, alkenyl, cycloalkyl, halogenoalkyl, aryl or arylalkyl, or $R^1$ is joined to $R^2$, and wherein X is —CONR$^2$—, —CSNR$^2$—, —NR$^1$-2CO—, —NR$^{12}$CS—, —NR$^{12}$CONR$^2$—,

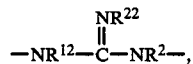

—SO$_2$NR$^2$— or —CO—, or, when $R^1$ is not hydrogen, is —NR$^{12}$COO—, —S—, —SO— or —SO$_2$—, wherein $R^2$ is hydrogen or alkyl, or $R^1$ and $R^2$ together form alkylene; wherein
$R^{12}$ is hydrogen or alkyl, and wherein
$R^{22}$ is hydrogen, cyano or nitro; or a salt thereof when appropriate. The compounds possess antioestrogenic activity and may be used for the treatment of hormone-dependent breast tumours or of anovulatory infertility.

9 Claims, No Drawings

ETHER AND ESTER DERIVATIVES OF PHENOLS

This invention relates to new phenol derivatives which possess antioestrogenic activity.

Various antioestrogens are now known. Two such compounds, tamoxifen and clomiphene, are commercially available, and others, for example nafoxidine, trioxifene and a number of compounds with code-numbers such as Cl 628 and LY 117018, have been the subject of clinical trials. Many oestrogenic compounds are also known, and in particular oestrogens based on hexoestrol bearing an amidic function, of the general formula:

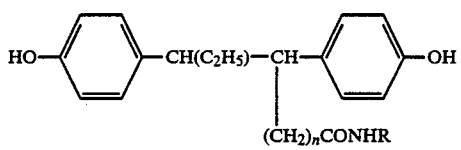

wherein n is 0 or 1 and R is hydrogen or alkyl, are described in the Journal of Medicinal Chemistry, 1982, 25, 1300-1307.

We have now found that certain phenol derivatives which are based on the hexoestrol nucleus but which bear an amidic or other function separated from the nucleus by an extended alkylene chain possess potent antioestrogenic activity.

According to the invention there is provided a phenol derivative of the formula:

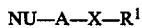

where NU is a mono- or bis-phenolic nucleus of the general formula:

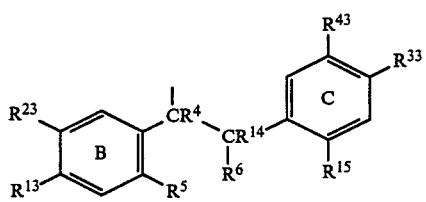

wherein one of $R^{13}$ and $R^{23}$, and/or one of $R^{33}$ and $R^{43}$, has the formula $R^3O$—, wherein $R^3$ is alkanoyl of up to 10 carbon atoms which bears one or two substituents selected from hydroxy, amino, alkylamino, dialkylamino, alkoxycarbonylamino, alkylthio, alkylsulphinyl, alkylsulphonyl, alkyldithio, carbamoyl, alkylcarbamoyl and dialkylaminoalkoxycarbonyl, wherein each alkyl or alkoxy has up to 6 carbon atoms; or $R^3$ is (azacycloalkyl)carbonyl or N-alkoxycarbonyl-(azacycloalkyl)carbonyl wherein the azacycloalkyl is of 5 to 7 ring atoms and the alkoxy is of up to 6 carbon atoms; or $R^3$ is alkanoyl of up to 10 carbon atoms which bears a carboxy substituent and one other substituent selected from those stated above; or $R^3$ is alkyl of up to 10 carbon atoms which bears an alkanoyloxy substituent or an alkanoyloxy substituent wherein the alkanoyl group itself bears one or two substituents selected from those stated above; or $R^3$ is sulphobenzoyl, 1-alkyl-1,4-dihydropyridinylcarbonyl or N-(sulphamoylphenyl)carbamoyl;

wherein if only one of $R^{13}$, $R^{23}$, $R^{33}$ and $R^{43}$ has the formula $R^3O$— another of $R^{13}$, $R^{23}$, $R^{33}$ and $R^{43}$ which is in the other aromatic ring B or C from that which contains the $R^3O$— substituent, is hydrogen, halogen, amino, trifluoromethyl, carboxy or carbamoyl, or alkyl, hydroxyalkyl, hydroxyfluoroalkyl, alkylamino, dialkylamino, alkanoylamino, alkanoyl, alkoxycarbonyl, alkylcarbamoyl, dialkylcarbamoyl, alkylsulphamoyl or dialkylsulphamoyl each of up to 6 carbon atoms, and wherein the other two of $R^{13}$, $R^{23}$, $R^{33}$ and $R^{43}$ are both hydrogen;

wherein $R^4$ and $R^{14}$, which may be the same or different, each is hydrogen or alkyl of up to 5 carbon atoms, or $R^4$ and $R^{14}$ are joined together so that $CR^4$-$CR^{14}$ is an olefinic double bond;

wherein either $R^5$ and $R^{15}$ are both hydrogen and $R^6$ is alkyl of up to 5 carbon atoms;

or $R^5$ and $R^6$ together form a direct link or —CH$_2$—, —CH(CH$_3$)—, —CH$_2$CH$_2$—, —(CH$_2$)$_3$—, —CH=CH—, —S—, —O—, —O—CR$_2$—, —O—CO—, —N-R—CH$_2$— or —N=CH— wherein R, the two values of which may be the same or different in —OCR$_2$—, is hydrogen or alkyl of up to 3 carbon atoms and $R^{15}$ is hydrogen; or $R^{15}$ and $R^6$ together form —CH$_2$— and $R^5$ is hydrogen;

and wherein the aromatic rings B and C each may optionally bear one or more halogen or alkyl substituents;

wherein A is straight- or branched-chain alkylene, alkenylene or alkynylene each of from 4 to 12 carbon atoms; or A has the formula:

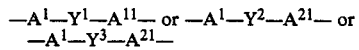

wherein $A^1$ and $A^{11}$ are each alkylene or alkenylene having together a total of 3 to 11 carbon atoms and $Y^1$ is —O—, —S—, —SO—, —SO$_2$— or —CO—; or $A^1$ is alkylene or alkenylene and $A^{21}$ is a direct link or alkylene, alkenylene or cycloalkylene, such that $A^1$ and $A^{21}$ together have a total of 2 to 10 carbon atoms, and $Y^2$ is —NRCO—, —CONR—, —COO— or —OCO—, wherein R has the meaning stated above, or $Y^3$ is phenylene, naphthylene or heterocyclene which may optionally bear one or more halogen or alkyl substituents, or heterocyclene which bears one or more alkoxy or oxo substituents, or A has the formula:

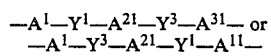

wherein $A^1$ and $A^{11}$ are each alkylene or alkenylene, and $A^{21}$ and $A^{31}$ are each a direct link or alkylene or alkenylene, such that $A^1$, $A^{21}$ and $A^{31}$ together, or $A^1$, $A^{21}$ and $A^{11}$ together, have a total of 1 to 9 carbon atoms, and $Y^1$ and $Y^3$ have the meanings stated above;

wherein $R^1$ is hydrogen, or alkyl, alkenyl, cycloalkyl, halogenoalkyl, aryl or arylalkyl each of up to 10 carbon atoms, or $R^1$ is joined to $R^2$ as defined below; and wherein X is —CONR$^2$—, —CSNR$^2$—, —NR$^{12}$CO—, —NR$^{12}$CS—, —NR$^{12}$CONR$^2$—,

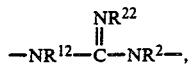

$$-NR^{12}-\overset{\overset{NR^{22}}{\|}}{C}-NR^{2}-,$$

—SO$_2$NR$^2$— or —CO—, or, when R$^1$ is not hydrogen, is —NR$^{12}$COO—, —S—, —SO— or —SO$_2$—, wherein R$^2$ is hydrogen or alkyl of up to 6 carbon atoms, or R$^1$ and R$^2$ together form alkylene such that, with the adjacent nitrogen atom, they form a heterocyclic ring of 5 to 7 ring atoms, one of which may be a second heterocyclic atom selected from oxygen, sulphur and nitrogen; wherein R$^{12}$ is hydrogen or alkyl of up to 6 carbon atoms; and wherein R$^{22}$ is hydrogen, cyano or nitro; or a salt thereof when appropriate.

It will be observed that except when R$^4$ and R$^{14}$ are joined together so that CR$^4$═CR$^{14}$ is an olefinic double bond, the phenol derivative of the invention possesses at least two asymmetric carbon atoms, namely those which bear the substituents R$^4$ and R$^{14}$, and it can therefore exist in racemic and optically-active forms. It is to be understood that this invention encompasses any racemic form of the phenol derivative, and any optically active form thereof, which possesses antioestrogenic activity, it being a matter of common general knowledge how a racemic compound may be separated into its optically-active forms, and how the antioestrogenic properties of any such form may be determined.

A suitable value for R$^{13}$, R$^{23}$, R$^{33}$ or R$^{43}$ when it is halogen or alkyl, or for the one or more optional halogen or alkyl substituents in ring B or C, or in the phenylene, naphthylene or heterocyclene group —Y$^3$— is, for example, fluoro, chloro, bromo, iodo, methyl, ethyl, isopropyl or isobutyl.

A suitable value for the optional alkoxy substituent in the heterocyclene group —Y$^3$— is, for example, methoxy or ethoxy.

A suitable value for R$^{13}$, R$^{23}$, R$^{33}$ or R$^{43}$ when it is hydroxyalkyl, hydroxyfluoroalkyl, alkylamino, dialkylamino, alkanoylamino, alkanoyl, alkoxycarbonyl, alkylcarbamoyl, dialkylcarbamoyl, alkylsulphamoyl or dialkylsulphamoyl is, for example, 1-hydroxyethyl, 2,2,2-trifluoro-1-hydroxy-1-trifluoroethyl, ethylamino, dimethylamino, acetamido, formyl, acetyl, propionyl, ethoxycarbonyl, methylcarbamoyl, diethylcarbamoyl, methylsulphamoyl, dimethylsulphamoyl or diethylsulphamoyl.

Preferably R$^{23}$ and R$^{43}$ are hydrogen and R$^{13}$ and R$^{33}$ have the formula R$^3$O—.

A preferred value for R$^3$ when it is substituted alkanoyl is, for example, alkanoyl derived from a naturally-occurring amino acid. Thus R$^3$ may be, for example, glycyl, alpha-L-aspartyl, L-seryl, L-methionyl, L-prolyl, N-t-butoxycarbonyl-L-methionyl, N-t-butoxycarbonyl-L-prolyl or the S-oxide of L-methionyl or N-t-butoxycarbonyl-L-methionyl. R$^3$ may also be 2-(methylthio)acetyl, 2-methylsulphinylacetyl, 2-(methylthio)propionyl, 2-methylsulphinylpropionyl, 2-amino-2-methylpropionyl or 2-benzyloxycarbonylamino-2-methylpropionyl.

A preferred value for R$^3$ when it is substituted alkyl is, for example, pivalyloxymethyl.

A suitable value for R, R$^4$ or R$^{14}$ when it is alkyl is, for example, methyl or ethyl. R and R$^4$ are preferably hydrogen and R$^{14}$ is preferably hydrogen or methyl, or R is hydrogen and R$^4$ and R$^{14}$ are joined together.

A suitable value for R$^6$ when it is alkyl is, for example, methyl, ethyl or n-propyl.

A suitable value for the heterocyclene group —Y$^3$— is, for example, a mono- or bi-cyclic divalent heterocyclic group which contains 1, 2 or 3 heteroatoms selected from nitrogen, oxygen and sulphur atoms, which may be fully saturated, partially saturated or unsaturated, which may be fused to a benzene ring, and which may bear one or more halogen, alkyl, alkoxy or oxo substituents. The free bonds may be attached to carbon atoms or nitrogen atoms. Particular heterocyclene groups are, for example, thien-2,5-ylene, thien-2,4-ylene, pyrazol-1,4-ylene, thiazol-2,5-ylene, 1,3,4-thiadiazol-2,5-ylene, 1,3,4-oxadiazol-2,5-ylene, piperidine-1,4-diyl and 1,4-piperazine-1,4-diyl.

One preferred value for the group —A— is a straight-chain alkylene group of the formula

$$-(CH_2)_n-$$

wherein n is an integer of from 4 to 12 especially from 5 to 11.

A second preferred value for the group A is a group of the formula

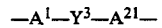

$$-A^1-Y^3-A^{21}-$$

wherein A$^1$ is straight-chain alkylene or alkenylene each of 2 to 9 carbon atoms, especially alkylene of 3 to 6 carbon atoms, —Y$^3$— is phenylene (ortho, meta- or, especially, para-) and A$^{21}$ is a direct link, methylene, ethylene, trimethylene or vinylene, especially ethylene.

A suitable value for R$^1$ when it is alkyl, alkenyl or cycloalkyl is, for example, methyl, ethyl, n-propyl, isopropyl, n-butyl, isobutyl, t-butyl, n-pentyl, isopentyl, t-pentyl, 2,2-dimethylpropyl, 1-methylbutyl, 2-methylbutyl, n-hexyl, 1,1-dimethylbutyl, 1,3-dimethylbutyl, n-heptyl, n-decyl, n-undecyl, allyl, cyclopentyl or cyclohexyl.

A suitable value for R$^1$ when it is aryl or aralkyl is, for example, phenyl, o-ethylphenyl, p-chlorophenyl, m-chlorophenyl, p-cyanophenyl, p-hydroxyphenyl, p-methoxyphenyl, benzyl, α-methylbenzyl, p-chlorobenzyl, p-methylbenzyl, 3,4-dichlorobenzyl, p-cyanobenzyl, p-methylthiobenzyl, p-trifluoromethylbenzyl, phenethyl, p-fluorophenethyl or p-chlorophenethyl.

A suitable value for R$^1$ when it is halogenoalkyl is, for example, 2-chloro-2,2-difluoroethyl, 2,2,2-trifluoroethyl, 1H,1H-heptafluorobutyl, 4,4,5,5,5-pentafluoropentyl or 1H,1H,2H,2H,3H,3H-heptafluorohexyl.

A suitable value for the heterocyclic ring —NR$^1$R$^2$ is, for example, pyrrolidino, piperidino, 4-methylpiperidino, 3-methylpiperidino, morpholino or 4-methylpiperazino.

A suitable value for R$^2$ or R$^{12}$ when it is alkyl is, for example, methyl, ethyl or n-butyl.

One appropriate salt is an acid-addition salt of a phenol derivative which possesses a basic function, for example a compound wherein R$^5$ and R$^6$ together form —NR—CH$_2$— or —N═CH— or wherein R$^3$ contains an amino group. A suitable acid-addition salt is, for example, a hydrochloride, hydrobromide, acetate, citrate, oxalate or tartrate.

Another appropriate salt is a base-addition salt of a phenol derivative which possesses a carboxy function, for example a compound wherein R$^3$ is a further substituted carboxyalkanoyl group. A suitable base-addition salt is, for example, a sodium, potassium, ammonium or cyclohexylamine salt.

A preferred phenol derivative of the invention has the formula stated above wherein both $R^3$ substituents have the preferred values stated above, wherein $R^{15}$ is hydrogen, wherein either $R^4$ is hydrogen and $R^{14}$ is hydrogen, methyl or ethyl, or $R^4$ and $R^{14}$ are joined together, wherein either $R^5$ is hydrogen and $R^6$ is methyl, ethyl or n-propyl, or $R^5$ and $R^6$ together form —CH$_2$—, —CH$_2$CH$_2$—, —CH(CH$_3$)—, —CH=CH— or —S—, wherein —A— is —(CH$_2$)$_n$—, wherein n is an integer from 4 to 12, especially from 5 to 11, or —A— is

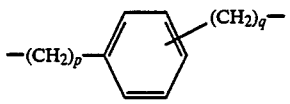

wherein p is an integer from 2 to 9, especially from 3 to 6, q is 0 to 3, especially 2, and the —(CH$_2$)$_q$-group is in the meta- or, especially, the para-position; wherein $R^1$ is alkyl or fluoroalkyl each of 4 to 10 carbon atoms, especially of 4 to 7 carbon atoms, or phenyl or chlorophenyl, or alkyl of 1 to 3 carbon atoms which bears a phenyl, tolyl, halogenophenyl or trifluoromethylphenyl substituent, or is linked to $R^2$ as stated below; wherein X is —CONR$^2$—, —S—, —SO— or —SO$_2$—, wherein $R^2$ is hydrogen or alkyl of up to 3 carbon atoms or together with $R^1$ forms alkylene of 5 or 6 carbon atoms; and wherein ring C may optionally bear one or two methyl substituents.

A particularly preferred phenol derivative of the invention has the formula stated above wherein the number of carbon atoms in the two groups A and $R^1$ adds up to between 11 and 21, especially 14 to 16 if neither $R^1$ nor A contains a phenyl or phenylene group, 17 to 19 if there is either a phenylene group in —A— or a phenyl group in $R^1$, and 19 to 21 if there are both a phenylene group in —A— and a phenyl group in $R^1$.

An especially preferred phenol derivative of the invention is a bis-$R^3$-ester or ether of a compound of the formula stated above wherein:

NU is 6-hydroxy-2-p-hydroxyphenylnaphth-1-yl and A is —(CH$_2$)$_9$—, —(CH$_2$)$_{10}$—, —(CH$_2$)$_{11}$— or —(CH$_2$)$_5$—(1,4-phenylene)—(CH$_2$)$_2$—;

or NU is 1,2,3,4-tetrahydro-6-hydroxy-2-p-hydroxyphenylnaphthyl-1-yl (either 1RS,2RS or 1RS,2SR isomer), or 1,2,3,4-tetrahydro-6-hydroxy-2-p-hydroxyphenyl-2-methylnaphth-1-yl (either 1RS,2RS or 1RS,2SR isomer), and A is —(CH$_2$)$_9$—, —(CH$_2$)$_{10}$—, —(CH$_2$)$_{11}$— or —(CH$_2$)$_4$—(1,4-phenylene)—(CH$_2$)$_2$—;

or NU is (1RS, 2RS)-5-hydroxy-2-p-hydroxyphenylindan-1-yl or (1RS, 2RS)-5-hydroxy-2-p-hydroxyphenyl-2-methylindan-1-yl and A is —(CH$_2$)$_9$—, —(CH$_2$)$_{10}$—, —(CH$_2$)$_{11}$— or —(CH$_2$)$_4$—(1,4-phenylene)—(CH$_2$)$_2$—; and wherein X is —CONR$^1$R$^2$ wherein $R^2$ is hydrogen or methyl and $R^1$ is n-butyl, 1H,1H-heptafluorobutyl, n-pentyl or n-hexyl, or X is —SR$^1$, SOR$^1$ or —SO$_2$R$^1$ wherein $R^1$ is n-pentyl, n-hexyl, 4,4,5,5,5-pentafluoropentyl, or 1H,1H,2H,2H,3H,3H-heptafluorohexyl.

Particularly preferred compounds are bis-pivalyloxymethyl ethers, or bis-aminoacyl esters derived from naturally-occurring amino-acids, or bis-(2-methylthio)acetyl, 2-methylsulphinylacetyl, 2-(methylthio)propionyl, 2-methylsulphinylpropionyl, 2-amino-2-methylpropionyl or 2-benzyloxycarbonylamino-2-methylpropionyl esters, of N-n-butyl, N-n-butyl-N-methyl, N-n-pentyl-, N-(1H,1H-heptafluorobutyl)- and N-(1H,1H-heptafluorobutyl)-N-methyl-3-p-[5-(6-hydroxy-2-p-hydrophenylnaphth-1-yl)pentyl]phenylpropionamide; (1RS,2RS)-1-{4-[p-(2-n-hexylthioethyl)phenyl]butyl}-2-p-hydroxyphenyl-1,2,3,4-tetrahydronaphth-6-ol and the corresponding 4,4,5,5,5-pentafluoropentylthio and 1H,1H,2H,2H,3H,3H-heptafluorohexylthio derivatives, and the corresponding hexylsulphinyl, hexylsulphonyl, heptafluorohexylsulphinyl and pentafluorohexylsulphinyl derivatives; 2-p-hydroxyphenyl-1-{5-[p-(2-n-hexylthioethyl)phenyl]pentyl}naphth-6-ol and the corresponding hexylsulphinyl derivative; N-methyl-N-(1H,1H-heptafluorobutyl)-3-p-{4-[(1RS,2RS)-6-hydroxy-2-p-hydroxyphenyl-2-methyl-1,2,3,4-tetrahydronaphth-1-yl]butyl}phenylpropionamide; (1RS,2RS)-1-{4-[p-(2-n-hexylthioethyl)phenyl]butyl}-2-p-hydroxyphenyl-2-methyl-1,2,3,4-tetrahydronaphth-6-ol and the corresponding 4,4,5,5,5-pentafluoropentylthio and 4,4,5,5,5-pentafluorohexylthio derivatives, and the corresponding hexylsulphinyl, pentafluoropentylsulphinyl and heptafluorohexylsulphinyl derivatives, and the corresponding (1RS,2SR) isomers of both the hexylthio and hexylsulphinyl derivatives; and (1RS,2RS)-1-[9-n-hexylthiononyl]-2-p-hydroxyphenyl-2-methyl-1,2,3,4-tetrahydronaphth-6-ol and the corrsponding 9-(4,4,5,5,5-pentafluoropentylthio)nonyl and 9-(1H,1H,2H,2H,3H,3H-heptafluorohexylthio)-nonyl derivatives, and the corresponding hexylsulphinyl, pentafluoropentylsulphinyl and heptafluorohexylsulphinyl derivatives, and the corresponding (1RS,2SR)-isomers of the six last-mentioned derivatives.

Specific phenol derivatives of the invention are hereinafter described in the Examples. Of these, preferred compounds are the bis-pivalyloxymethyl ethers of both the (1RS,2RS)- and (1RS,2SR)-isomers of both 1,2,3,4-tetrahydro-2-p-hydroxyphenyl-2-methyl-1-[9-(4,4,5,5,5-pentafluoropentylsulphinyl)nonyl]naphth-6-ol and 1-[9-(1H,1H,2H,2H,3H,3H-heptafluorohexylsulphinyl)-nonyl]-1,2,3,4-tetrahydro-2-p-hydroxyphenyl-2-methylnaphth-6-ol; and the bis-2-methylsulphinylacetyl and bis-2-benzyloxycarbonylamino-2-methylpropionyl esters of (1RS,2RS)-1,2,3,4-tetrahydro-2-p-hydroxyphenyl-2-methyl-1-[9-(4,4,5,5,5-pentafluoropentylsulphinyl)nonyl]naphth-6-ol.

A preferred process for the manufacture of a phenol derivative of the invention comprises the reaction of a compound of the formula NU$^1$—A—X—R$^1$ wherein A, X and $R^1$ have the meanings stated above and wherein NU$^1$ has the same meaning as is stated above for NU except that one or two of $R^{13}$, $R^{23}$, $R^{33}$ and $R^{43}$ are hydroxy, the other three or two of $R^{13}$, $R^{23}$, $R^{33}$ and $R^{43}$ having meanings stated above other than $R^3$O—, with an alkylating or acylating agent of the formula $R^3$—Z$^1$, wherein $R^3$ has the meaning stated above and Z$^1$ is an activated group.

When $R^3$ is substituted alkanoyl, a suitable compound $R^3$—Z$^1$ is an acid anhydride, mixed anhydride, acyl halide or the acid of the formula $R^3$—OH in the presence of a carbodiimide.

When $R^3$ is substitued alkyl a suitable value for Z$^1$ is a halogeno group, for example the iodo group.

The starting material of the formula NU$^1$—A—X—R$^1$ is described in published European Specification No. 124369 or in one or other of our copending applicationSer. Nos. 726,824 or 726,822 (based on UK Applications Nos. 8410899 or 8410900).

A phenol derivative of the invention wherein X is —SO— or —SO$_2$— may be obtained by the oxidation of the corresponding compound wherein X is —S—. The conditions for the oxidation will be chosen to provide the desired product; for example aqueous sodium metaperiodate will oxidise the sulphur group to sulphinyl, and m-chloroperbenzoic acid in chloroform solution will oxidise the sulphur group to sulphonyl.

As stated above, a phenol derivative of the invention possesses antioestrogenic activity. This may be demonstrated by its effect in antagonising the increase in weight of the uterus of an immature female rat produced by administering oestradiol benzoate to said rat. Thus, when a phenol derivative of the invention and oestradiol benzoate are co-administered for 3 days to such a rat, a smaller increase in uterine weight is produced than the substantial increase which would be produced by the administration of oestradiol benzoate without the phenol derivative of the invention.

In particular, a preferred phenol derivative of the invention produces an antioestrogenic effect at a dose which produces no partial agonist effect, unlike the known antioestrogens tamoxifen and clomiphene. When a preferred phenol is coadministered with oestradiol benzoate to a rat as described above, no increase in uterine weight whatsoever is observed at a suitable dose.

When used to produce an anti-oestrogenic effect in warm-blooded animals, a typical daily dose is from 0.1 to 25 mg/kg. administered orally or by injection. In man this is equivalent to an oral dose of from 5 to 1250 mg./day. A phenol derivative of the invention is most conveniently administered to man in the form of a pharmaceutical composition.

According to a further feature of the invention, there is provided a pharmaceutical composition comprising a phenol derivative of the invention together with a pharmaceutically acceptable diluent or carrier.

The composition may be in a form suitable for oral or parenteral administration. A tablet or capsule is a particularly convenient form for oral administration and such a composition may be made by conventional methods and contain conventional excipients. Thus a tablet could contain diluents, for example mannitol or maize starch, disintegrating agents, for example alginic acid, binding agents, for example methyl-cellulose, and lubricating agents, for example magnesium stearate.

The composition may contain, in addition to the phenol derivative of the invention, one or more other agents which inhibit or antagonise hormonal action, for example antiandrogenic agents, for example flutamide, antiprogestational agents, or aromatase inhibitors, for example aminoglutethimide.

A composition for oral administration may conveniently contain from 5 to 500 mg. of a phenol derivative of the invention.

The invention is illustrated but not limited by the following Examples. In these, all the final compounds were non-crystalline and all their structures were confirmed by proton magnetic resonance and/or mass spectroscopy. The diphenolic starting material for Examples 1, 3, 4 and 9 is described in Example 3 (Table 2) of European Specification No. 124369, that for Examples 2, 5 and 6 in Example 8 (Table 2) or (for the hexylsulphinyl compound of Example 2) Example 9 (Table 2) of said European Specification. The starting materials for Examples 10 and 11 were prepared by similar processes to those described in Example 7 and Example 8 (Table 6) of said European Specification, except that 9-(dimethyl-t-butylsilyloxy)non-1-yne was used used as intermediate in place of the corresponding dec-1-yne. Separation of (1RS, 2RS) and (1RS, 2SR) isomers was by chromatography on a silica gel column using a 17:3 v/v mixture of toluene and ethyl acetate as eluent.

EXAMPLE 1

Pivalyloxymethyl iodide [3.7 ml. of a solution of pivalyloxymethyl chloride (0.185 g.) and sodium iodide (1.0 g.) in acetone (20 ml.)] was added to a stirred mixture of N-(1H,1H-heptafluorobutyl)-3-p-[5-(6-hydroxy-2-p-hydroxyphenylnaphth-1-yl)pentyl]phenyl-N-methylpropionamide (0.1 g.) and potassium carbonate (0.043 g.) in acetone (5 ml.) and the mixture was stirred at laboratory temperature for 18 hours and then evaporated to dryness. The residue was purified by chromatography on a silica gel column using a 10:1 v/v mixture of toluene and ethyl acetate as eluent and there was thus obtained as an oil N-(1H,1H-heptafluorobutyl)-N-methyl-3-p-[5-(6-pivalyloxymethoxy-2-p-pivalyloxymethoxyphenylnaphth-1-yl)pentyl]phenylpropionamide.

EXAMPLE 2

The process described in Example 1 was repeated using pivalyloxymethyl iodide and either (1RS,2RS)-1-{4-[p-(2-hexylthioethyl)phenyl]butyl}-1,2,3,4-tetrahydro-2-p-hydroxyphenylnaphth-6-ol or the corresponding 2-hexylsulphinylethyl analogue as starting materials. There were thus obtained (1RS,2RS)-1-{4-[p-(2-hexylthioethyl)phenyl]butyl}-1,2,3,4-tetrahydro-6-pivalyloxymethoxy-2-p-pivalyloxymethoxyphenylnaphthalene and (1RS,2RS)-1-{4-[p-(2-hexylsulphinylethyl)phenyl]butyl}-1,2,3,4-tetrahydro-6-pivalyloxymethoxy-2-p-pivalyloxymethoxyphenylnaphthalene.

EXAMPLE 3

4-Dimethylaminopyridine (0.01 g.) and a solution of N,N¹-dicyclohexylcarbodiimide (0.07 g.) in methylene chloride (1 ml.) were successively added to a stirred solution of N-(1H,1H-heptafluorobutyl)-3-p-[5-(6-hydroxy-2-p-hydroxyphenylnaphth-1-yl)pentyl]-N-methylpropionamide (0.1 g.) and N-benzyloxycarbonylglycine (0.07 g.) in methylene chloride (10 ml.) which was maintained under an atmosphere of argon, and the mixture was stirred at laboratory temperature for 12 hours and then filtered. The filtrate was evaporated to dryness and the residue was purified by chromatography on a silica gel column using a 5:1 v/v mixture of toluene and ethyl acetate as eluent. The product obtained was stirred with diethyl ether and the mixture was filtered.

A mixture of the solid bis-N-benzyloxycarbonylglycinyl ester thus obtained (0.05 g.) ethanol (5 ml.), ethyl acetate (5 ml.), saturated ethereal hydrogen chloride solution (0.05 ml.) and a 10% palladium-on-charcoal catalyst (0.025 g.) was stirred at laboratory temperature under an atmosphere of hydrogen for 16 hours and then filtered, and the filtrate was evaporated to dryness. The residue was stirred with diethyl ether and the mixture was filtered. There was thus obtained as solid residue 3-p-[5-(6-glycycloxy-2-p-glycyloxyphenylnaphth-1-yl)pentyl]phenyl-N-(1H,1H-heptafluorobutyl)-N-methylpropionamide dihydrochloride.

EXAMPLE 4

The process described in Example 3 was repeated using either beta-O-benzyl-N-benzyloxycarbonyl-L-aspartic acid or O-t-butoxycarbonyl-N-benzyloxycarbonyl-L-serine in place of N-benzyloxycarbonylglycine. The O-benzyl and N-benzyloxycarbonyl protecting groups were removed by hydrogenolysis as described in Example 3, and the O-t-butoxycarbonyl protecting group was removed by hydrolysis with aqueous trifluoroacetic acid. There were thus obtained 3-p[5-(6-alpha-L-aspartyloxy-2-p-alpha-L-aspartyloxyphenylnaphth-1-yl)pentyl]phenyl-N-(1H,1H-heptafluorobutyl)-N-methylpropionamide dihydrochloride and N-(1H,1H-heptafluorobutyl)-N-methyl-3-p-[5-(6-L-seryloxy-2-p-L-seryloxyphenylnaphth-1-yl)pentyl]-phenylpropionamide dihydrochloride.

EXAMPLE 5

4-Dimethylaminopyridine (0.01 g.) and a solution of N,N$^1$-dicyclohexylcarbodiimide (0.2 g.) in methylene chloride (2 ml.) were successively added to a stirred solution of (1RS,2RS)-1-{4-[p-(2-hexylthioethyl)-phenyl]butyl}-1,2,3,4-tetrahydro-2-p-hydroxyphenyl-naphth-6-ol (0.2 g.) and N-t-butoxycarbonyl-L-methionine (0.21 g.) in methylene chloride (10 ml.) which was maintained under an atmosphere of argon, and the mixture was stirred at laboratory temperature for 12 hours and then filtered. The filtrate was evaporated to dryness and the residue was purified by chromatography on a silica gel column using a 5:1 v/v mixture of toluene and ethyl acetate as eluent. There was thus obtained as an oil (1RS,2RS)-1-{4-[p-(2-hexylthioethyl)phenyl]butyl}-1,2,3,4-tetrahydro-6-(N-t-butoxycarbonyl-L-methionyloxy)-2-p-(N-t-butoxycarbonyl-L-methionyloxy)-phenylnaphthalene.

EXAMPLE 6

The process described in Example 5 was repeated using N-t-butoxycarbonyl-L-proline in place of N-t-butoxycarbonyl-L-methionine. There was thus obtained (1RS,2RS)-1-{4-[p-(2-hexylthioethyl)phenyl]butyl}-1,2,3,4-tetrahydro-6-(N-t-butoxycarbonyl-L-prolyloxy)-2-p-(N-t-butoxycarbonyl-L-prolyloxy)phenylnaphthalene.

EXAMPLE 7

A saturated solution of hydrogen chloride in diethyl ether (2 ml.) and then water (0.01 ml.) were successively added to a solution of (1RS,2RS)-1-{4-[p-(2-hexylthioethyl)phenyl]butyl}-1,2,3,4-tetra-hydro-6-(N-t-butoxycarbonyl)-L-prolyoxy-2-p(N-t-butoxycarbonyl)-L-prolyloxyphenylnaphthalene (Example 6; 0.115 g.) in diethyl ether (10 ml.), and the mixture was stirred under an atmosphere of argon at laboratory temperature for 16 hours and then evaporated to dryness. The residue was stirred with a 9:1 v/v mixture of diethyl ether and ethanol and the mixture was filtered. There was thus obtained as solid residue (1RS,2RS)-1-{4-[p-(2-hexylthioethyl)phenyl]butyl}-6-prolyloxy-2-p-L-prolyloxyphenyl-1,2,3,4-tetrahydronaphthalene.

EXAMPLE 8

A solution of sodium metaperiodate (0.16 g.) in water (1 ml.) was added to a stirred solution of the hexylthioethyl compound prepared according to Example 5 or Example 6 (0.15 g.) in methanol (10 ml.) and the mixture was stirred at laboratory temperature for 16 hours and then evaporated to dryness. The residue was extracted three times with methylene chloride (10 ml. each time) and the combined extracts were dried and evaporated to dryness. The residue was purified by chromatography on a silica gel column using a 50:1 v/v mixture of methylene chloride and methanol as eluant. There were thus obtained as oils:

(1RS,2RS)-1-{4-[p-(2-hexylsulphinylethyl)phenyl]-butyl}-1,2,3,4-tetrahydro-6-(4-methylsulphinyl-2-(S)-t-butoxycarbonylaminobutyryloxy)-2-p-(4-methylsulphinyl-2-(S)-t-butoxycarbonylaminobutyryloxy)phenylnaphthalene; and (1RS,2RS)-1-{4-[p-(2-hexylsulphinylethyl)phenyl]-butyl}-1,2,3,4-tetrahydro-6-(N-t-butoxycarbonyl-L-prolyloxy)-2-p-(N-t-butoxycarbonyl-L-prolyloxy)-phenylnaphthalene.

EXAMPLE 9

The process described in the first part of Example 3 was repeated except that N-t-butoxycarbonyl-L-methionine was used in place of N-benzyloxycarbonylglycine. The product obtained was oxidised with sodium metaperiodate by a similar process to that described in Example 8 and there was thus obtained as an oil N-(1H,1H-heptafluorobutyl)-N-methyl-3-p-{5-[6-(4-methylsulphinyl-(2S)-2-t-butoxycarbonylaminobutyryloxy)-2-p-(4-methylsulphinyl-(2S)-2-t-butoxycarbonylaminobutyryloxy)phenylnaphth-1-yl]pentyl}phenylpropionamide.

EXAMPLE 10

The process described in Example 1 was repeated using as diphenolic starting material either the (1RS, 2RS) or (1RS, 2SR) isomer of either 1-[9-(4,4,5,5,5-pentafluoropentylthio)nonyl]- or 1-[9-(1H,1H,2H,2H,3H,5H-heptafluorohexylthio)nonyl]-2-p-hydroxyphenyl-2-methyl-1,2,3,4-tetrahydronaphth-6-ol. The products obtained were oxidised with sodium metaperiodate by a similar process to that described in Example 8. There were thus obtained as oils the compounds described in the following table:

[Chemical structure diagram showing a tetrahydronaphthalene with XR$^1$ and (CH$_2$)$_9$ substituents, OCH$_2$OCOC(CH$_3$)$_3$ and (CH$_3$)$_3$CCOOCH$_2$O groups, and CH$_3$]

| X | R$^1$ | Isomer |
|---|---|---|
| S | (CH$_2$)$_3$C$_2$F$_5$ | 1RS, 2RS |
| S | (CH$_2$)$_3$C$_2$F$_5$ | 1RS, 2SR |
| SO | (CH$_2$)$_3$C$_2$F$_5$ | 1RS, 2RS |
| SO | (CH$_2$)$_3$C$_2$F$_5$ | 1RS, 2SR |
| S | (CH$_2$)$_3$CF$_2$CF$_2$CF$_3$ | 1RS, 2RS |
| S | (CH$_2$)$_3$CF$_2$CF$_2$CF$_3$ | 1RS, 2SR |
| SO | (CH$_2$)$_3$CF$_2$CF$_2$CF$_3$ | 1RS, 2RS |
| SO | (CH$_2$)$_3$CF$_2$CF$_2$CF$_3$ | 1RS, 2SR |

EXAMPLE 11

The process described in the first part of Example 3 was repeated except that (1RS, 2RS)-2-p-hydroxyphenyl-2-methyl-1-[9-(4,4,5,5,5-pentafluoropentylthio)-nonyl]-1,2,3,4-tetrahydronaphth-6-ol and either 2-benzyloxycarbonylamino-2-methylpropionic acid, 2-(methylthio)acetic acid or 2-(methylthio)propionic acid were used as starting materials. There were thus respectively obtained, as oils, after purification by chromatography on a silica gel column using a 9:1 v/v mixture of toluene and ethyl acetate as eluent:

(1RS,2RS)-2-p-(2-benzyloxycarbonylamino-2-methylpropionyloxy)phenyl-6-(2-benzyloxycarbonylamino-2-methylpropionyloxy)-2-methyl-1-[9-(4,4,5,5,5-penta-fluoropentylthio)nonyl]-1,2,3,4-tetrahydronaphthalene;

(1RS,2RS)-2-methyl-6-[2-(methylthio)acetoxy]-2-p-[2-(methylthio)acetoxy]phenyl-1-[9-(4,4,5,5,5-pentafluoropentylthio)nonyl]-1,2,3,4-tetrahydronaphthalene; and (1RS,2RS)-2-methyl-6-[2-(methylthio)propionyloxy]-2-p-[2-(methylthio)propionyloxy]phenyl-1-[9-(4,4,5,5,5-pentafluoropentylthio)nonyl]-1,2,3,4-tetrahydronaphthalene.

The above three compounds were oxidised with sodium metaperiodate by a similar process to that described in Example 8, and there were thus respectively obtained, as oils;

(1RS,2RS)-2-p-(2-benzyloxycarbonylamino-2-methylpropionyloxy)phenyl-6-(2-benzyloxycarbonylamino-2-methylprionyloxy)-2-methyl-1-[9-(4,4,5,5,5-penta-fluoropentylsulphinyl)nonyl]-1,2,3,4-tetrahydronaphthalene;

(1RS,2RS)-2-methyl-6-(2-methylsulphinylacetoxy)-2-p-(2-methylsulphinylacetoxy)phenyl-1-[9-(4,4,5,5,5-pentafluoropentylsulphinyl)nonyl]-1,2,3,4-tetrahydronaphthalene; and (1RS,2RS)-2-methyl-6-(2-methylsulphinylpropionyloxy)-2-p-(2-methylsulphinylpropionyloxy)phenyl-1-[9-(4,4,5,5,5-pentafluoropentylsulphinyl)nonyl]-1,2,3,4-tetrahydronaphthalene.

The 2-(methylthio)propionic acid used as a starting material was obtained by the reaction of 2-(methylthio)acetic acid (0.5 g.) and methyl iodide (0.74 g.) in the presence of lithium diisopropylamide (prepared from 6.5 ml. of a 1.6 molar solution of n-butyllithium and 1.04 g. of diisopropylamine) in tetrahydrofuran initially at −70° C. and finally at laboratory temperature. The oily product was purified by chromatography on a silica gel column using a 9:1 v/v mixture of methylene chloride and methanol as eluent.

What we claim is:

1. A phenol derivative of the formula:

where NU is a mono- or bis-phenolic nucleus of the formula

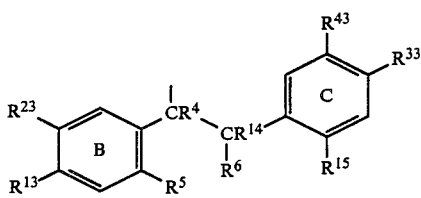

wherein one of $R^{13}$ and $R^{23}$, and one of $R^{33}$ and $R^{43}$, has the formula $R^3O-$, wherein $R^3$ is alkanoyl of up to 10 carbon atoms which bears one or two substituents selected from hydroxy, amino, alkylamino, dialkylamino, alkoxycarbonylamino, alkylthio, alkylsulphinyl and alkylsulphonyl, wherein each alkyl or alkoxy has up to 6 carbon atoms; or $R^3$ is (azacycloalkyl)carbonyl or N-alkoxycarbonyl (azacyloalkyl)carbonyl wherein the azacycloalkyl is of 5 to 7 ring atoms and the alkoxy is of up to 6 carbom atoms; or $R^3$ is alkanoyl of up to 10 carbon atoms which bears a carbosy substituent and one other substituent selected from hydroxy, amino, alkylamino, dialkylamino, alkoxycarbonylamino, alkylthio, alkylsulphinyl and alkylsulphonyl, wherein each alkyl or alkoxy has up to 6 carbon atoms; or $R^3$ is alkyl of up to 10 carbon atoms which bears an alkanoyloxy substituent or an alkanoyloxy substituent wherein the alkanoyl group itself bears one or two substituents selected from hydroxy, amino, alkylamino, dialkylamino, alkoxycarbonylamino, alkylthio, alkylsulphinyl and alkylsulphonyl, wherein each alkyl or alkoxy has up to 6 carbon atoms;

and wherein the other two of $R^{13}$, $R^{23}$, $R^{33}$ and $R^{43}$ are both hydrogen;

wherein $R^4$ and $R^{14}$, which may be the same or different, each is hydrogen or alkyl of up to 5 carbon atoms, or $R^4$ and $R^{14}$ are joined together so that $CR^4-CR^{14}$ is an olefinic double bond;

wherein $R^5$ and $R^6$ together form a direct link or $-CH_2-$, $-CH(CH_3)-$, $-CH_2CH_2-$, $-(CH_2)_3-$ or $-CH=CH-$ and $R^{15}$ is hydrogen;

and wherein the aromatic rings B and C each may optionally bear one or more halogen or alkyl substituents;

wherein A is straight- or branched-chain alkylene, alkenylene or alkynylene each of from 4 to 12 carbon atoms; or A has the formula: $-A^1-Y^3-A^{21}-$ wherein $A^1$ is alkylene or alkenylene and $A^{21}$ is a direct link or alkylene, alkenylene or cycloalkylene, such that $A^1$ and $A^{21}$ together have a total of 2 to 10 carbon atoms, and $Y^3$ is phenylene or naphthalene which may optionally bear one or more halogen or alkyl substituents, wherein $R^1$ is alkyl, alkenyl, cycloalkyl, halogenoalkyl, phenyl, chlorophenyl, o-ethylphenyl, p-cyanophenyl, p-hydroxyphenyl, p-methoxyphenyl alkyl of 1 to 3 carbon atoms which bears a phenyl, tolyl, halogenophenyl or trifluoromethylphenyl substituent, alpha-methylbenzyl, 3,4-dichlorobenzyl, p-cyanobenzyl or p-methylthiobenzyl; and wherein X is $-CONR^2-$, $-S-$, $-SO-$ or $-SO_2-$, wherein $R^2$ is hydrogen or alkyl of up to 6 carbon atoms, or $R^1$ and $R^2$ together with the adjacent nitrogen atom form a heterocyclic ring of 5 to 7 ring atoms, one of which may be a second heterocyclic atom selected from oxygen, sulphur and nitrogen; or a salt thereof when appropriate.

2. A phenol derivative as claimed in claim 1 wherein $R^{15}$, $R^{23}$ and $R^{43}$ are all hydrogen; wherein $R^{13}$ and $R^{33}$ both have the formula $R^3O-$ wherein $R^3$ is alkanoyl of up to 10 carbon atoms which bears one or two substituents selected from hydroxy, amino, alkoxycarbonylamino, alkylthio and alkylsulphinyl wherein each alkyl or alkoxy has up to 6 carbon atoms, or which bears one carboxy substituent and one of the last-mentioned substituents, or $R^3$ is prolyl or N-alkoxycarbonylprolyl, or pivaloyloxymethyl; wherein either $R^4$ is hydrogen and $R^{14}$ is hydrogen, methyl or ethyl, or $R^4$ and $R^{14}$ are joined together so that $CR^4-CR^{14}$ is an olefinic double bond; wherein $R^5$ and $R^6$ together form $-CH_2-$, $-CH(CH_3)-$, $-CH_2CH_2-$ or $-CH=CH-$; wherein the aromatic rings B and C either bear no further substituent or bear one or more fluoro, methyl or ethyl substituents;

wherein the group —A— is a straight chain alkylene group of the formula

wherein n is an integer of from 4 to 12 or the group A is a group of the formula:

wherein $A^1$ is straight-chain alkylene of 2 to 9 carbon atoms, —$Y^3$— is phenylene and $A^{21}$ is a direct link, methylene, ethylene, or trimethylene and the $A^{21}$ group is in the meta- or para-position;
wherein X is —$CONR^2$—, —S—, —SO— or —$SO_2$—;
wherein either $R^1$ is methyl, ethyl, n-propyl, isopropyl, n-butyl, isobutyl, t-butyl, n-pentyl, isopentyl, t-pentyl, 2,2-dimethylpropyl, 1-methylbutyl, 2-methylbutyl, n-hexyl, 1,1-dimethylbutyl, 1,3-dimethylbutyl, n-heptyl, n-decyl, allyl, cyclopentyl, cyclohexyl, phenyl, o-ethylphenyl, p-chlorophenyl, m-chlorophenyl, p-cyanophenyl, p-hydroxyphenyl, p-methoxyphenyl, benzyl, alpha-methylbenzyl, p-chlorobenzyl, p-methylbenzyl, 3,4-dichlorobenzyl, p-cyanobenzyl, p-methylthiobenzyl, p-trifluoromethylbenzyl, phenethyl, p-fluorophenethyl, p-chlorophenethyl, 2-chloro-2,2-difluoroethyl, 1H, 1H-heptafluorobutyl, 4,4,5,5,5-pentafluoropentyl or 1H,1H,2H,2H,3H,3H-heptafluorohexyl and $R^2$ is hydrogen, methyl, ethyl or n-butyl, or —$NR^1R^2$ is pyrrolidino, piperidino, 4-methylpiperidino, 3-methylpiperidino, morpholino or 4-methylpiperazino;
or a salt thereof.

3. A phenol derivative as claimed in claim 1 wherein $R^{15}$, $R^{23}$ and $R^{43}$ are all hydrogen, wherein $R^{13}$ and $R^{33}$ both have the formula $R^3O$— wherein $R^3$ is alkanoyl of up to 10 carbon atoms which bears one or two substituents selected from hydroxy, amino, alkoxycarbonylamino, alkylthio and alkylsulphinyl wherein each alkyl or alkoxy has up to 6 carbon atoms, or which bears one carboxy substituent and one of the last-mentioned substituents, or $R^3$ is prolyl or N-alkoxycarbonylprolyl, or pivaloyloxymethyl, wherein $R^4$ is hydrogen and $R^{14}$ is hydrogen, methyl or ethyl, or $R^4$ and $R^{14}$ are joined together, wherein $R^5$ and $R^6$ together form —$CH_2$—, —$CH_2CH_2$—, —$CH(CH_3)$— or —CH=CH—. wherein —A— is —$(CH_2)_n$—, wherein n is an integer from 4 to 12, or —A— is

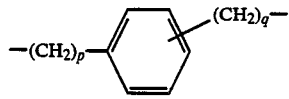

wherein p is an integer from 2 to 9, q is 0 to 3, and the —$(CH_2)_q$-group is in the meta- or para-position; wherein $R^1$ is alkyl or fluoroalkyl each of 4 to 10 carbon atoms, or phenyl or chlorophenyl, or alkyl of 1 to 3 carbon atoms which bears a phenyl, tolyl, halogenophenyl or trifluoromethylphenyl substituent, or is linked to $R^2$ as stated below; wherein X is —$CONR^2$—, —S—, —SO— or —$SO_2$—, wherein $R^2$ is hydrogen or alkyl of up to 3 carbon atoms or together with $R^1$ forms alkylene of 5 or 6 carbon atoms; and wherein the aromatic ring C as otherwise defined in claim 1 may optionally bear one or two methyl substituents.

4. A phenol derivative as claimed in claim 1 wherein the number of carbon atoms in the two groups A and $R^1$ adds up to 14 to 16 if neither $R^1$ nor A contains a phenyl or phenylene group, 17 to 19 if there is either a phenylene group in —A— or a phenyl group in $R^1$, and 19 and 21 if there are both a phenylene group in —A— and a phenyl group in $R^1$.

5. A phenol derivative as claimed in claim 1 which is a bis-$R^3$- ester or ether, wherein $R^3$ is alkanoyl of up to 10 carbon atoms which bears one or two substituents selected from hydroxy, amino, alkoxycarbonyl-amino, alkthio and alkylsulphinyl wherein each alkyl or alkoxy has up to 6 carbon atoms, or which bears one carboxy substituent and one of the last mentioned substituents, or $R^3$ is prolyl or N-alkoxycarbonylprolyl, or pivaloyloxymethyl, or a compound of the formula stated in claim 1 wherein:
NU is 6-hydroxy-2-p-hydroxyphenylnaphth--yl and A is —$(CH_2)_9$—, —$(CH_2)_{10}$—, —$(CH_2)_{11}$— or —$(CH_2)_5$—(1,4-phenylene)—$(CH_2)_2$—;
or NU is 1,2,3,4-tetrahydro-6-hydroxy-2-p-hydroxyphenylnaphthyl-1-yl (either 1RS, 2RS or 1RS, 2SR isomer), or 1,2,3,4-tetrahydro-6-hydroxy-2-p-hydroxy-phenyl-2-methylnaphth-1-yl (either 1RS, 2RS or 1RS, 2SR isomer), and A is —$(CH_2)_9$—, —$(CH_2)_{10}$—, —$(CH_2)_{11}$— or —$(CH_2)_4$—(1-4-phenylene)—$(CH_2)_2$—;
or NU is (1RS)-5-hydroxy-2-p-hydroxy-phenylindan-1-yl or (1RS, 2RS)-5-hydroxy-2-p-hydroxy-phenyl-2-methylindan-1yl and A is —$(CH_2)_9$—, —$(CH_2)_{10}$—, —$(CH_2)_{11}$— or —$(CH_2)_4$—(1,4-phenylene)—$(CH_2)_2$—; and wherein X is —$CONR^1R^2$ wherein $R^2$ is hydrogen or methyl and $R^1$ is n-butyl, 1H,1H-heptafluorobutyl, n-pentyl or n-hexyl, or X is —$SR^1$ or —$SO_2R^1$ wherein $R^1$ is n-pentyl, n-hexyl, 4,4,5,5,5-penta-fluoropentyl, or 1H,1H,2H,2H,3H,3H-heptafluorohexyl.

6. A pharmaceutical composition having antiestrogenic properties comprising an effective amount of a phenol derivative, claimed in claim 1 together with a pharmaceutically acceptable diluent or carrier.

7. A method for producing an antioestrogenic effect in a warm-blooded animal in need of such treatment, which comprises administering to said animal an effective amount of a phenol derivative as claimed in claim 1.

8. A compound selected from the group of compounds consisting of the bis-pivalyloxymethyl ethers of both the (1RS,2RS)- and (1RS,2SR)- isomers of both 1,2,3,4-tetrahydro-2-p-hydroxyphenyl-2-methyl-1[9-(4,4,5,5,5-pentafluoropentylsulphinyl)nonyl]naphth-6-ol and 1-[9-(1H,1H,2H,2H,3H,3H-heptafluorohexyl-sulphinyl)nonyl]-1,2,3,4,-tetrahydro-2-p-hydroxyphenyl-2-methylnaphth-6-ol; and the bis-2-methysulphinylacetyl and bis-2-benzyloxy-carbonylamino-2-methylpropionyl esters of (1RS,2RS)-1,2,3,4-tetrahydro-2-p-hydroxyphenyl-2-methyl-1-[9-(4,4,5,5,5-pentafluoropentylsulphinyl)nonyl]naphth-6-ol.

9. A compound selected from the group of compounds consisting of bis-pivalyloxymethyl ethers, bis-glycyl, alpha-L-aspartyl, L-seryl, L-methionyl, L-prolyl, N-t-butoxycarbonyl-L-methionyl, N-t-butoxycarbonyl-L-prolyl, the S-oxide of L-methionyl and N-t-butoxycarbonyl-L-methionyl esters and bis-(2-methylthio)acetyl, 2-methylsulphinylacetyl, 2-(methylthio)-propionyl, 2-methylsulphinylpropionyl, 2-amino-2-methylpropionyl and 2-benzyloxycarbonylamino-2-methylpropionyl esters of N-n-butyl-, N-n-butyl-N-methyl-, N-n-pentyl-, N-(1H,1H-heptafluorobutyl)- and N-(1H,1H-heptafluorobutyl)-N-methyl-3-p-[5-(6-hydroxy-2-p-hydroxyphenylnaphth-1-yl)pentyl]-phenylpropionamide, (1RS,2RS)-1-{4-[p-(-n-hexylthioethyl)phenyl]butyl}-2-p-hydroxyphenyl-1,2,3,4-tetrahydronapth-6-ol, (1RS,2RS)-1,2,3,4-tetrahydro-2-p-hydroxyphenyl-1-{4-[p-(2-(4,4,5,5,5-pentafluoropentylthio)ethyl)phenyl]butyl} naphth-6-ol, (1RS,2RS)-1-{4-[p-(2-(1H,1H,2H,2H,3H,3H-heptafluorohexylthio)ethyl)phenyl]-butyl}-2-p-hydroxyphenyl-1,2,3,4-tetrahydronaphth-6-ol, (1RS,2RS)-1-{4-[p-(2-n-hexylsulphinylethyl)phenyl]butyl{-2-p-hydroxyphenyl-1,2,3,4-tetrahydronaphth-6ol, (1RS,2RS)-1-{4-[p-(2-n-hexylsulphonylethyl)phenyl]butyl}-2-p-hydroxyphenyl-1,2,3,4-tetrahydronaphth-6-ol, (1RS,2RS)-1,2,3,4-tetrahydro-2-p-hydroxyphenyl-1-{4-[p-(2-(4,4,5,5,5,-pentafluoropentyl sulphinyl)ethyl)phenyl]butyl}naphth-6-ol and (1RS,2RS)-1-{4-[p-(2-(1H,1H,2H,2H,3H,3H-heptafluorohexylsulphinyl)ethyl)-phenyl]butyl}-2-p-hydroxyphenyl-1,2,3,4-tetrahydronaphth-6-ol; 1-{5-[p-(2-n-hexylthioethyl)phenyl]pentyl}-2-(p-hydroxyphenyl) naphth-6ol and 1-{5-[p-(2-n-hexylsulphinylethyl)phenyl] pentyl}-2-(p-hydroxyphenyl)naphth-6-ol; N-(1H,1H-heptafluorobutyl)-N-methyl-3-p-{4-[(1RS,2RS)-6-hydroxy-2-p-hydroxyphenyl-2-methyl-1,2,3,4-tetrahydronaphth-1-yl]butyl}-phenylpropionamide; (1RS,2RS)-1-{4-[p-(2-n-hexylthioethyl)phenyl]butyl}-2-p-hydroxyphenyl-2-methyl-1,2,3,4-tetrahydronaphth-6-ol and the (1RS,2SR)-isomer; (1RS,2RS)-1,2,3,4-tetrahydro-2-p-hydroxyphenyl-2-methyl-1-{4-[p-(2-(4,4,5,5,5-pentafluoropentylthio)ethyl) phenyl]butyl}naphth-6ol, (1RS,2RS)-1-{4-[p-(2-(1H,1H,2H,2H, 3H,3H-heptafluorohexylthio)ethyl)phenyl]butyl}-2-p-hydroxyphenyl-2-methyl-1,2,3,4-tetrahydronaphth-6-ol, (1RS,2RS)-1-{4-[p-(2-n-hexylsulphinylethyl)phenyl]butyl}-2-p-hydroxyphenyl-2-methyl-1,2,3,4-tetrahydronaphth-6-ol and the (1RS,2SR)-isomer, (1RS,2RS)-1,2,3,4-tetrahydro-2-p-hydroxyphenyl-2-methyl-1-{4-[p-(2-(4,4,5,5,5-pentafluoropentylsulphinyl)ethyl)phenyl]butyl}naphth-6-ol and (1RS,2RS)-1-{4-[p-(2-(1H,1H,2H,2H,3H,3H-heptafluorohexylsulphinyl)ethyl)-phenyl]butyl}-2-p-hydroxyphenyl-2-methyl-1,2,3,4-tetrahydronaphth-6ol; (1RS,2RS)-1-[9-n-hexylthiononyl]-2-p-hydroxyphenyl-2-methyl-1,2,3,4-tetrahydronaphth-6ol and the (1RS,2SR)-isomer, (1RS,2RS)-1,2,3,4-tetrahydro-2-p-hydroxyphenyl-2-methyl-1-[9-(4,4,5,5,5,-pentafluoropentylthio)nonyl]-naphth-6-ol and the (1RS,2SR)-isomer, (1RS,2RS)-1-[9-(1H,1H,2H,2H,3H,3H-heptafluorohexylthio)nonyl]-2-p-hydroxyphenyl-2-methyl-1,2,3,4-tetrahydronaphth-6ol and the (1RS,2SR)-isomer, (1RS,2RS)-1-[9-n-hexylsulphinylnonyl]-2p-hydroxyphenyl-2-methyl-1,2,3,4-tetrahydronaphth-6-ol and the (1RS,2SR)-isomer, (1RS,2RS)-1,2,3,4-tetrahydro-2-p-hydroxyphenyl-2-methyl-1-[9-(4,4,5,5,5-pentafluoropentylsulphinyl)-nonyl]naphth-6-ol and the (1RS,2SR)-isomer and (1RS,2RS)-1-9-(1H,1H,2H,2H,3H,3H-heptafluorohexylsulphinyl)nonyl]-2-p-hydroxyphenyl-2-methyl-1,2,3,4-tetrahydronaphth-6ol and the (1RS,2SR) isomer.

* * * * *